United States Patent [19]

Burckhardt

[11] Patent Number: 4,791,134
[45] Date of Patent: Dec. 13, 1988

[54] MILBEMYCIN DERIVATIVES AND THE USE THEREOF IN PEST CONTROL

[75] Inventor: Urs Burckhardt, Basel, Switzerland

[73] Assignee: Ciba-Geigy Corporation, Ardsley, N.Y.

[21] Appl. No.: 741,041

[22] Filed: Jun. 4, 1985

[30] Foreign Application Priority Data

Jun. 8, 1984 [CH] Switzerland ............... 2808/84

[51] Int. Cl.$^4$ ................ C07D 493/22; A61K 31/365
[52] U.S. Cl. .................................. 514/450; 549/264; 546/15
[58] Field of Search ............... 549/264; 514/450

[56] References Cited

U.S. PATENT DOCUMENTS 3,950,360  4/1976  Aoki et al.
4,346,171  8/1982  Takiguchi et al.

*Primary Examiner*—Norma S. Milestone
*Attorney, Agent, or Firm*—Edward McC. Roberts; Meredith C. Findlay

[57] ABSTRACT

The invention relates to milbemycin derivatives of formula I

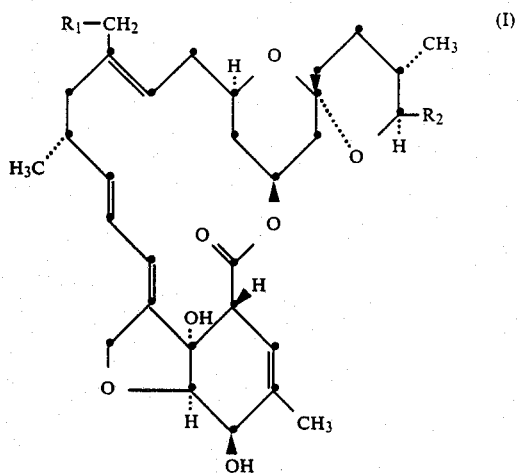

wherein $R_1$ is an aliphatic or aromatic radical or is a pyridyl ring or a heterocyclic oxygen-containing 5- or 6-membered ring, all of which may also be bound through oxygen, and $R_2$ is methyl, ethyl or isopropyl. These compounds are suitable for controlling arthropode species such as injurious insects or endo- or ectoparasites of animals and are employed in the form of compositions. The compounds can also be used as intermediates for obtaining further milbemycin derivatives.

12 Claims, No Drawings

MILBEMYCIN DERIVATIVES AND THE USE THEREOF IN PEST CONTROL

The present invention relates to milbemycin derivatives of the formula I, to the preparation of said derivatives and to the use thereof as intermediates for obtaining further milbemycin derivatives. The invention further relates to the use of the novel compounds for controlling pests and to pesticidal compositions which contain the compounds of formula I as active ingredients.

Specifically, the present invention relates to milbemycin derivatives of the formula I,

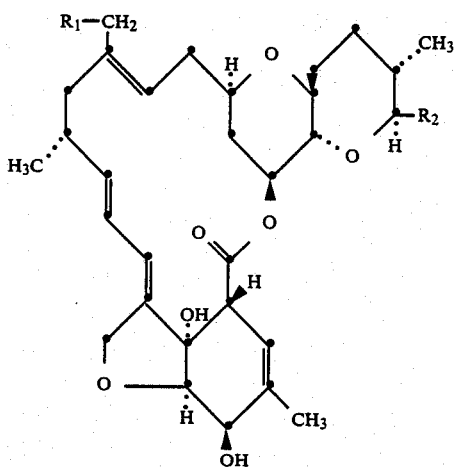

wherein $R_1$ is a straight chain or branched alkyl or alkoxy group, each of which is unsubstituted or substituted by one or more members selected from the group consisting of halogen, hydroxy and alkoxy; or is an alkenyl, alkenyloxy, alkynyl or alkynyloxy group, each of which is unsubstituted or substituted by alkoxy; or is a phenyl, phenoxy or benzyl group, each of which is unsubstituted or substituted in the aromatic ring by one or more members selected from the group consisting of halogen, alkyl and alkoxy; or is a pyridyl group, a pyridylalkyl group or a pyridyloxy group which is bound through a carbon atom, each of which is unsubstituted or substituted as indicated for phenyl; or is a 2,2-dimethyl-1,3-dioxolanylmethoxy radical, a furfuryl, furfuryloxy, tetrahydrofurfuryl, tetrahydrofurfuryloxy, dihydropyrane or tetrahydropyrane radical; or is a dihydropyranemethyl or tetrahydropyranemethyl radical, a dihydropyranemethoxy or tetrahydropyranemethoxy radical; or is a chlorine or bromine atom; and $R_2$ is methyl, ethyl or isopropyl.

Halogen in the definitions of the above substituents denotes fluorine, chlorine, bromine or iodine. A halogen-substtuted hydrocarbon radical can preferably carry 1 to 5 halogens.

An alkyl, alkenyl or alkynyl group which is bound direct or through an oxygen atom preferably contains up to 18 carbon atoms and a lower aliphatic group contains up to 6 carbon atoms.

Most preferably an alkyl, alkenyl or alkynyl group contains up to 8 carbon atoms and a lower aliphatic group up to 4 carbon atoms.

Depending on the indicated number of carbon atoms, alkyl by itself or as moiety of an alkoxy group is, for example, a member selected from the following group of radicals of shorter chain length: methyl, ethyl, propyl, butyl, pentyl, hexyl, heptyl, octyl etc. and the isomers thereof, e.g. isopropyl, isobutyl, sec-butyl, tert-butyl, isopentyl, etc.

Examples of halogenated alkyl radicals (also as moiety of an alkoxy group) are: $CH_2Cl$, $CHCl_2$, $CHF_2$, $CH_2F$, $CCl_3$, $CH_2Br$, $CH_2CF_3$, $CF_2CH_2F$, $CH_2CH_2Br$, $CF_3$, $CH_2$—$CCl_2$—$CF_3$, $CH_2I$—$CH_3$ etc.

Throughout this specification, the term "alkenyl" denotes simply unsaturated or polyunsaturated hydrocarbon radicals, for example 1-propenyl, allyl, 1-butenyl, 2-butenyl, 3-butenyl, butadienyl, pentadienyl, etc., and also in particular the hydrocarbon radicals:

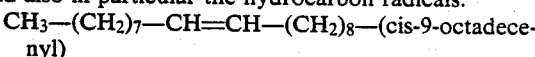
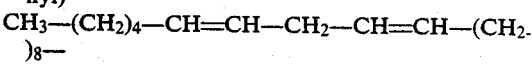

which are bound direct or through oxygen.

Substituted phenyl or pyridyl radicals are preferably those which contain one or more members selected from fluorine, chlorine, methyl and methoxy.

A preferred group of compounds comprises those of the formula I, wherein $R_1$ is a $C_1$-$C_4$alkyl group. Among these compounds, those compounds are preferred in which $R_1$ is methyl or ethyl.

Also preferred are those compounds in which $R_1$ is chlorine or bromine.

Another preferred group of compounds comprises the compounds of formula I, wherein $R_1$ is an ether group. Among these compounds, those compounds are preferred in which $R_1$ is an unsubstituted or a halogenated $C_1$-$C_4$alkoxy group, as well as those in which $R_1$ is $C_2$-$C_6$hydroxyalkoxy.

The compounds of formula I are preeminently suitable for controlling pests of animals and plants, including ecto- and endoparasites of animals, and are at the same time versatile intermediates for obtaining further derivatives of milbemycin.

Milbemycins are macrolides of the formula III

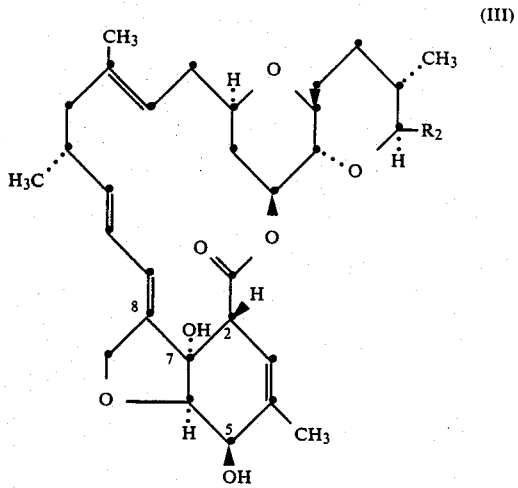

(wherein $R_2$ is methyl, ethyl or isopropyl) which are formed from certain streptomyces species. Reference is made in this connection to U.S. Pat. No. 3,950,360, in which milbemycin $A_3$ [$R_2$=methyl] and milbemycin $A_4$ [$R_2$=ethyl] are described; and to U.S. Pat. No.

4,346,171, in which milbemycin D [$R_2$=isopropyl] is described.

Milbemycin derivatives of formula I can be obtained from compounds of the formula II, wherein $R_2$ is methyl, ethyl or isopropyl, and X is chlorine or bromine

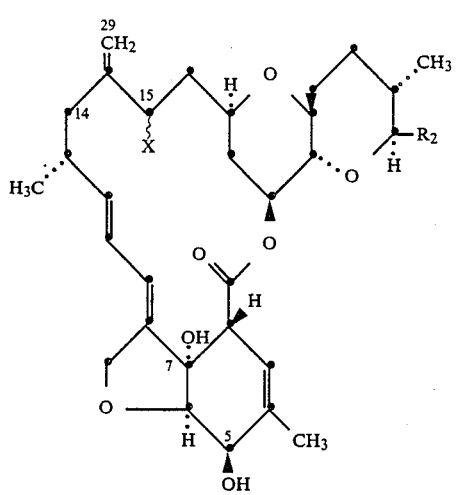

(II)

by etherification or alkylation at position 29, without having to protect the secondary and tertiary OH group in positions 5 and 7. The 14,29-double bond is displaced to the 14,15-position. Milbemycin derivatives are in general susceptible to bases and have a propensity to epimerise in position 2.

Compounds of formula I are prepared according to this invention as follows:

(a) to obtain compounds of formula I, wherein $R_1$ is a radical which is bound through a carbon radical: by reacting the compound of formula II with an organocuprate which contains the radical $R_1$ which it is desired to introduce, in the temperature range from $-70°$ to $0°$ C., preferably from $-60°$ to $-20°$ C., in an inert gas atmosphere; and (b) to obtain compounds of formula I, wherein $R_1$ is a radical which is bound through an oxygen atom: by reacting the compound of formula II with the corresponding alcohol $R_1$—OH in the manner of a Koenigs-Knorr synthesis, in the presence of a silver salt as condensing agent, in the temperature range from $-20°$ to $+40°$ C., preferably from $-5°$ to $+25°$ C., with the exclusion of light, or in the presence of a copper(I) trifluoromethanesulfonate as condensing agent and in the same temperature range; and (c) to obtain compounds of formula I, wherein $R_1$ is chlorine or bromine: by treating the compound of formula II with a silver salt catalyst in the presence of $Cl^\ominus$ or $Br^\ominus$ ions.

(Process a): Organocuprates react in the manner of the reaction course observed by K. Oshima et al., J. Am. Chem. Soc. 95, 7927 [1973], when coupling with allylic halides, by attacking compound II in position 29 to split off the halide ion in position 15 and displacing the double bond to the 14,15-position. As organocuprates it is possible to use in principle all known reagents of this type [q.v. G. H. Posner: "Substitution Reactions using organocopper reagents", Organic Reactions, Vol. 22, 253–400 (1975)] such as $R_1$—Cu $R_1$—Cu—ligand (ligand denotes a group that does not participate in the reaction, e.g. a phosphine, sulfide or an oxidation product thereof), or organocopper reagents that contain a second metal atom such as Pb, Zn, Hg, Mg, B, Al, but preferably Li, for example organolithium cuprates of the type $(R_1)_2CuLi$ and, preferably, of the type $(R_1)_2Cu(CN)Li_2$.

Suitable solvents are inert solvents, for example ethereal compounds such as tetrahydrofuran, dioxan, dialkyl ethers, or hydrocarbons, or mixtures of both types.

Nitrogen or a rare gas, e.g. argon, may be used as inert gas.

(Process b): The alcoholysis of the allylic halide of formula II to give the derivatives which are etherified in position 29 proceeds only very reluctantly with the alcohol component R—OH alone, even at the reflux temperature of the reaction mixture. On the other hand, the reaction rate is greatly improved by carrying out the reaction in the presence of a silver salt as condensing agent, e.g. $Ag_2O$, $Ag_2CO_3$ or $CF_3$—COOAg. The reaction proceeds satisfactorily in the presence of freshly distilled $Ag_2O$. The preferred silver salt is silver trifluoromethanesulfonate ($CF_3SO_3Ag$), in the presence of which the etherification proceeds rapidly and at low temperature (room temperature and below). Also preferred are trifluoromethanesulfonates of other metals, for example $Cu(I)CF_3SO_3$, which, as benzene complex, speeds up the etherification, with allylic rearrangement, in desired manner and at low temperature. Suitable solvents are the alcohol to be etherified, and also ethers and ethereal compounds (dioxan, tetrahydrofuran, dimethoxyethane), ketones such as acetone or methyl ethyl ketone, hydrocarbons such as petroleum ether, benzene, toluenes or halogenated hydrocarbons such as chlorobenzene or dichloromethane, or mixtures of such solvents.

(Process c): In the presence of a silver salt catalyst and of $Cl^\ominus$ and $Br^\ominus$ ions, allyl halide derivatives of formula II form compounds of formula I, wherein $R_1$ is chlorine or bromine. This reaction can take place concurrently in the course of the etherification reaction (b). The reaction products must be separated from each other by physicochemical methods, for example by column chromatography or layer chromatography. Suitable solvents are those indicated for (b) above.

Preparation of the starting material of formula II, $\Delta^{29,14}$-15H-15-chloromilbemycin, from corresponding milbemycin derivatives of formula III 2.23 g (4 mM) of milbemycin D ($R_2$=isopropyl) are dissolved at room temperature in 100 ml of analytically pure dichloromethane and to this solution is added a solution of 820 mg (8 mM) of $Ca(OCl)_2$ (about 70%) in 10 ml of distilled water. With efficient stirring, small pieces of solid $CO_2$ are added to the resultant suspension from time to time in order to liberate the hypochlorous acid, which amounts in all to about three times the stoichiometrically required amount. The reaction is complete after 2½ to 3 hours. The phases are separated and the organic phase is dried over Na$_2$SO$_4$, filtered, and concentrated, affording 2.3 g (85% of theory) of Δ$^{29,14}$-15H-15-chloromilbemycin D (R$_2$=isopropyl) with a melting point of 137°–140° C. (decomp.).

The corresponding milbemycin A$_3$ derivative of formula II (R$_2$=methyl), can be prepared in the same manner; mol. wt. 563.13. Mass spectrum m/e: 562 (M+), 434, 312, 181, 151.

In the same manner it is possible to obtain the corresponding milbemycin A$_4$ derivative of formula II (R$_2$=ethyl); mol. wt. 577.16. Mass spectrum m/e: 576 (M+), 448, 312, 195, 167, 151.

The compounds of formula I can be prepared from these Δ$^{29,14}$-15H-15-chloromilbemycins in accordance with the following Examples.

PREPARATORY EXAMPLE 1

29-n-Butylmilbemycin D (compound 1.5)

Under dry conditions and in an atmosphere of argon, 269 mg (3.0 mM) of CuCN are charged to a reactor and then 3 ml of tetrahydrofuran are added dropwise. With stirring, the suspension is cooled to −80° C. and 3.75 ml (6.0 mM) of n-butyl lithium in 2 ml of hexane are added dropwise. The reaction mixture is warmed briefly to 0° C. to give a clear solution which is immediately cooled again to −50° to −60° C. Then a solution of 591 mg (1.0 mM) of Δ$^{29,14}$-15H-15-chloromilbemycin D in 6 ml of tetrahydrofuran is added dropwise, whereupon the macrolide reacts with the (nC$_4$H$_9$)$_2$Cu(CN)Li$_2$ now present in the solution. A red solution forms temporarily over 10 minutes and is stirred for 1½ hours at −50° C. and then 5 ml of a saturated 9:1 solution of NH$_4$Cl in concentrated NH$_4$OH is added. The mixture is extracted with three 5 ml portions of diethyl ether and the combined ethereal phases are dried over sodium sulfate, filtered and concentrated by evaporation. The crude product is purified by flash and thick layer chromatography (eluant: 20:1 mixture of dichloromethane/methanol), affording 98 mg (16% of theory) of amorphous compound 1.5; mol. wt. 612.85. Mass spectrum m/e: 612 (M+), 484, 466, 412, 370, 334, 304.

PREPARATORY EXAMPLE 2

29-Methylmilbemycin D (compound 1.1)

Under dry conditions and in an atmosphere of argon, 269 mg (3.0 mM) of CuCN are charged to a reactor and then 3 ml of tetrahydrofuran are added dropwise. With stirring, the suspension is cooled to −80° C. and 132 ml (6.0 mM) of methyl lithium in 2 ml of diethyl ether are added dropwise. The reaction mixture is warmed briefly to 0° C. to give a clear solution which is immediately cooled again to −50° to −60° C. Then a solution of 591 mg (1.0 mM) of Δ$^{29,14}$-15H-15-chloromilbemycin D in 6 ml of tetrahydrofuran is added dropwise, whereupon the macrolide reacts with the (CH$_3$)$_2$Cu(CN)Li$_2$ now present in the solution. A red solution forms temporarily over 10 minutes and is stirred for 1½ hours at −50° C. and then 5 ml of a saturated 9:1 solution of NH$_4$Cl in concentrated NH$_4$OH is added. The mixture is extracted with three 5 ml portions of diethyl ether and the combined ethereal phases are dried over sodium sulfate, filtered and concentrated by evaporation. The residue is purified by flash chromatography (eluant: 20:1 mixture of dichloromethane/methanol), affording 100 mg (17% of theory) of amorphous compound 1.1; mol. wt. 570.77. Mass spectrum m/e: 570 (M+), 442, 273, 209, 181, 151.

The compounds listed in Table 1 can be prepared in the same manner.

TABLE 1

| | C—C bonds | | | |
|---|---|---|---|---|
| No. | R$_1$ | R$_2$ | Mol. wt. | Mass spectrum m/e |
| 1.1 | CH$_3$ | isoC$_3$H$_7$ | 570.77 | 570, 442, 273, 209, 181, 151 |
| 1.2 | C$_2$H$_5$ | isoC$_3$H$_7$ | 585.46 | |
| 1.3 | sec-C$_4$H$_9$ | isoC$_3$H$_7$ | 612.85 | 612, 484, 466, 315, 209, 181, 151 |
| 1.4 | tert-C$_4$H$_9$ | isoC$_3$H$_7$ | 612.85 | 612, 484, 466, 315, 209, 181, 151 |
| 1.5 | n-C$_4$H$_9$ | isoC$_3$H$_7$ | 612.85 | 612, 484, 466, 412, 370, 334, 304 |
| 1.6 | —C(=CH$_2$)—OCH$_3$ | isoC$_3$H$_7$ | | |
| 1.7 | CH$_3$ | CH$_3$ | 541.38 | |
| 1.8 | CH$_3$ | C$_2$H$_5$ | 556.74 | 556, 428, 420, 278, 259 |
| 1.9 | C$_6$H$_5$ | isoC$_3$H$_7$ | 632.84 | 632, 534, 504, 335, 209, 181, 151 |
| 1.10 | —C$_6$H$_4$Cl(4) | isoC$_3$H$_7$ | | |
| 1.11 | —C$_6$H$_3$Cl$_2$(2,4) | isoC$_3$H$_7$ | | |
| 1.12 | —C$_6$H$_3$Cl$_2$(2,3) | isoC$_3$H$_7$ | | |
| 1.13 | —C$_6$H$_3$Cl$_2$(2,3) | CH$_3$ | | |
| 1.14 | —C$_6$H$_3$Cl$_2$(2,3) | C$_2$H$_5$ | | |
| 1.15 | —C$_6$H$_3$(CH$_3$)$_2$(2,3) | CH$_3$ | | |
| 1.16 | —CH$_2$—C$_6$H$_5$ | CH$_3$ | | |
| 1.17 | —CH$_2$—C$_6$H$_5$ | isoC$_3$H$_7$ | 646.87 | 646, 518, 368, 349, 209, 181, 159 |
| 1.18 | 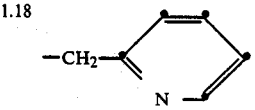 | CH$_3$ | | |
| 1.19 | 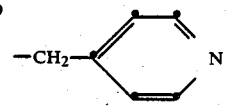 | C$_2$H$_5$ | | |
| 1.20 | 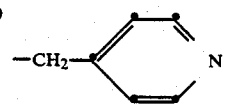 | isoC$_3$H$_7$ | 647.86 | 647, 629, 611, 519, 497, 370 |
| 1.21 | 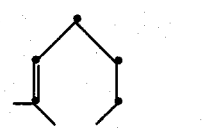 | isoC$_3$H$_7$ | | |
| 1.22 | 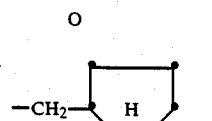 | CH$_3$ | | |

TABLE 1-continued

| | C—C bonds | | | |
|---|---|---|---|---|
| No. | R₁ | R₂ | Mol. wt. | Mass spectrum m/e |
| 1.23 | 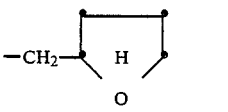 —CH₂— | C₂H₅ | | |
| 1.24 | 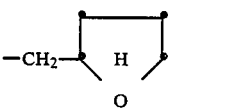 —CH₂— | isoC₃H₇ | | |
| 1.25 | 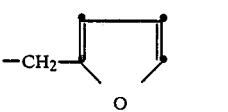 —CH₂— | isoC₃H₇ | | |
| 1.26 | 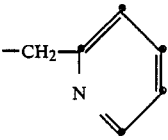 —CH₂— | isoC₃H₇ | 647.86 | 647, 629, 496, 160, 93 |

PREPARATORY EXAMPLE 3

29-Methoxymilbemycin D (compound 2.3)

29-Chloromilbemycin D (compound 3.3)

With the exclusion of light, 890 mg (1.505 mM) of $\Delta^{29,14}$-15H-15-chloromilbemycin D and 425 mg (1.656 mM) of silver trifluoromethanesulfonate (silver triflate) are dissolved in 50 ml of methanol and the solution is stirred for 15 hours at room temperature. After filtration, the reaction solution is rapidly concentrated by evaporation in vacuo at 30° C. and the residue is taken up in diethyl ether. The ethereal solution is washed three times with a saturated solution of NaCl and three times with a saturated solution of NaHCO₃, dried over sodium sulfate, filtered and concentrated by evaporation. The crude product is purified by flash chromatography (eluant: 100:0.5 mixture of dichloromethane/methanol) and thick layer chromatography (eluant: 1:1 mixture of dichloromethane/diethyl ether), affording two amorphous main products:

(a) 91 g (10% of theory) of 29-methoxymilbemycin D, mol. wt. 586.77. Mass spectrum m/e: 586 (M+), 458, 440, 181, 151;

(b) 192 mg (21% of theory) of 29-chloromilbemycin D; mol. wt. 591.18. Mass spectrum m/e: 590 (M+), 462, 293, 209, 181, 151.

PREPARATORY EXAMPLE 4

29-(2',2',2'-Trifluoroethoxy)milbemycin D (compound 2.27)

With exclusion of light, 591 mg (1.0 mM) of $\Delta^{29,14}$-15H-15-chloromilbemycin D and 283 mg (1.1 mM) of silver triflate in 10 ml of trifluoroethanol are stirred for 2 hours at room temperature. To the resultant dark solution are added 10 ml of a saturated solution of NaHCO₃ and 5 ml of dichloromethane. After shaking, the phases are separated. The organic phase is washed once with a saturated solution of NaCl and purified by thick layer chromatography (2 mm plates; elution with a 20:1 mixture of dichloromethane/methanol), affording 88 mg (14% of theory) of 29-(2',2',2'-trifluoroethoxy)milbemycin D; mol. wt. 654.78. Mass spectrum m/e: 654 (M+), 590, 526, 462, 209, 181, 151.

The compounds of Table 2 and those of Table 3 (29-halomilbemycins) are obtained in accordance with Examples 3 and 4 using a corresponding alcoholic or phenolic compound in the presence of a silver salt.

TABLE 2

| | Ether derivatives | | | |
|---|---|---|---|---|
| No. | R₁ | R₂ | Mol. wt. | Mass spectrum m/e |
| 2.1 | —OCH₃ | CH₃ | | |
| 2.2 | —OCH₃ | C₂H₅ | | |
| 2.3 | —OCH₃ | isoC₃H₇ | 586.77 | 586, 458, 440, 181, 151 |
| 2.4 | —OC₂H₅ | CH₃ | | |
| 2.5 | —OC₂H₅ | isoC₃H₇ | 600.80 | 600, 472, 454, 426, 408, 209, 181, 151 |
| 2.6 | —OC₃H₇(iso) | isoC₃H₇ | 614.83 | 614, 486, 209, 181, 151 |
| 2.7 | —OC₄H₉(tert.) | isoC₃H₇ | 628.85 | 628, 426, 293, 209, 181, 151 |
| 2.8 | —OCH₂—CH=CH₂ | isoC₃H₇ | 612.81 | 612, 484, 466, 426, 408, 209 |
| 2.9 | —OCH₂—CH=CH—CH₃(cis) | isoC₃H₇ | | |
| 2.10 | —O—(CH₂)₈—CH=CH—(CH₂)₇—CH₃(cis) | CH₃ | | |
| 2.11 | —O—(CH₂)₈—CH=CH—(CH₂)₇—CH₃(cis) | C₂H₅ | | |
| 2.12 | —O—(CH₂)₈—CH=CH—(CH₂)₇—CH₃(cis) | isoC₃H₇ | | |
| 2.13 | —O—(CH₂)₈CH=CH—CH₂—CH=CH(CH₂)₄CH₃(cis,cis) | isoC₃H₇ | | |
| 2.14 | —O(CH₂)₈(CH=CH—CH₂)₃—CH₃ | C₂H₅ | | |
| 2.15 | —OCH₂—C≡CH | CH₃ | | |
| 2.16 | —OCH₂—C≡CH | C₂H₅ | | |
| 2.17 | —OCH₂—C≡CH | isoC₃H₇ | | |
| 2.18 | —O—C₆H₅ | isoC₃H₇ | | |
| 2.19 | —O—C₆H₄Cl(2) | isoC₃H₇ | | |
| 2.20 | —O—C₆H₄Cl(4) | isoC₃H₇ | | |
| 2.21 | —O—C₆H₃(CH₃)₂(2,3) | CH₃ | | |
| 2.22 | —O—C₆H₃(CH₃)₂(2,3) | C₂H₅ | | |
| 2.23 | —O—C₆H₃(CH₃)₂(2,3) | isoC₃H₇ | | |
| 2.24 | —O—C₆H₄OCH₃(3) | isoC₃H₇ | | |
| 2.25 | —O—C₆H₄CH₃(4) | isoC₃H₇ | | |
| 2.26 | —OCH₂—C₆H₅ | isoC₃H₇ | | |
| 2.27 | —OCH₂—CF₃ | isoC₃H₇ | 654.78 | 654, 590, 526, 462, 209, 181, 151 |
| 2.28 | —OCH₂—CF₃ | CH₃ | | |
| 2.29 | —OCH₂—CF₃ | C₂H₅ | | |
| 2.30 | —OCH₂—CCl₂—CF₃ | C₂H₅ | | |
| 2.31 | —OCH₂—CF₂—CH₂F | CH₃ | | |
| 2.32 | —OCH₂—CH₂—OH | isoC₃H₇ | 616.80 | 616, 488, 470, 426, 408, 209, 181, 149 |

TABLE 2-continued

| No. | R₁ | R₂ | Mol. wt. | Mass spectrum m/e |
|---|---|---|---|---|
| | | Ether derivatives | | |
| 2.33 | —OCH₂—CH₂—OH | C₂H₅ | | |
| 2.34 | —OCH₂—CH₂—OH | CH₃ | | |
| 2.35 | —OCH₂—CH₂—OCH₃ | isoC₃H₇ | 630.83 | 630, 426, 408, 209, 181, 149 |
| 2.36 | —OCH₂-(pyridyl) | isoC₃H₇ | | |
| 2.37 | —OCH₂-(phenyl) | isoC₃H₇ | | |
| 2.38 | —OCH₂-(tetrahydropyranyl, H) | C₂H₅ | | |
| 2.39 | —OCH₂-(dihydrofuranyl) | isoC₃H₇ | 652.83 | 652, 571, 524, 506, 355, 209, 181, 151 |
| 2.40 | —OCH₂-(tetrahydrofuranyl, H) | isoC₃H₇ | 656.86 | 656, 638, 426, 408, 209, 181, 151 |
| 2.41 | —OCH₂-(2,2-dimethyl-1,3-dioxolanyl) (d,l) | isoC₃H₇ | 689.89 | 686, 671, 408, 254, 209, 181, 151 |
| 2.42 | —OCH₂-(2,2-dimethyl-1,3-dioxolanyl) (d,l) | C₂H₅ | | |
| 2.43 | —OCH₂-(2,2-dimethyl-1,3-dioxolanyl) (d,l) | CH₃ | | |
| 2.44 | —OCH₂—CHOH—CH₂—OH | isoC₃H₇ | 646, 628, 518, 500, 426, 408 | |

TABLE 3

29-Halomilbemycins

| No. | R₁ | R₂ | Mol. wt. | Mass spectrum m/e |
|---|---|---|---|---|
| 3.1 | Cl | CH₃ | | |
| 3.2 | Cl | C₂H₅ | | |
| 3.3 | Cl | isoC₃H₇ | 591.18 | 590, 462, 293, 209, 181, 151 |
| 3.4 | Br | CH₃ | | |
| 3.5 | Br | C₂H₅ | | |
| 3.6 | Br | isoC₃H₇ | | |

The compounds of formula I are most effective against pests of the families Ixodidae, Dermanyssidae, Sarcoptidae, Psoroptidae; of the orders Mallophaga, Siphonoptera, Anoptera (e.g. Haematopinidae family); and of the order Diptera, in particular pests of the families Muscidae, Calliphoridae, Oestrididae, Tabanidae, Hippoboscidae and Gastrophilidae.

The compounds of formula I cn also be used against hygiene pests, especially of the order Diptera including the families Sarcophagiae, Anophilidae and Culicidae; of the order Orthoptera (e.g. the Blattidae family), and of the order Hymenoptera (e.g. Formicidae family).

The compounds of formula I also have lasting action against mites and insects which are parasites of plants.

When used to control spider mites of the order Acarina, they are effective against eggs, nymphs and adults of Tetranychidae (Tetranychus spp. and Panonychus spp). They also have excellent activity against sucking insects of the order Homoptera, in particular against pests of the families Aphididae, Delphacidae, Cicadellidae, Psyllidae, Loccidae, Diaspididae and Eriophyidae (e.g. the rust mite on citrus fruit); of the orders Hemiptera,, Heteroptera and Thysanoptera; and against plant-destructive insects of the orders Lepidoptera, Coleoptera, Diptera and Orthoptera.

The compounds of formula I are also suitable for use as soil insecticides against pests in the soil.

The compounds of formula I are therefore effective against all development stages of sucking and eating insects in crops such as cereals, cotton, rice, maize, soybeans, potatoes, vegetables, fruit, tobacco, hops, citrus fruit, avocados and others.

The compounds of formula I are also effective against plant nematodes of the species Meloidogyne, Heterodera, Pratylenchus, Ditylenchus, Radopholus, Rhizoglyphus and others.

Furthermore, the compound of formula I act against helminths, among which the endoparasitic nematodes can be the cause of severe diseases in mammals and fowl, for example in sheep, pigs, goats, cattle, horses, donkeys, dogs, cats, guinea pigs, cage-birds. Typical nematodes having this indication are: Haemonchus, Trichostrongylus, Ostertagia, Nematodirus, Cooperia, Ascaris, Bunostromum, Oesophagostromum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris.

Certain species of the genera Nematodirus, Cooperia and Oesophagostomum attack the intestinal tract of the host animal, whereas others of the species Haemonchus and Ostertagia parasiticise in the stomach and those of the species Dictyocaulus in the lung tissue. Parasites of the families Filariidae and Setariidae are found in internal cell tissue and internal organs, e.g. in the heart, blood vessels, lymph vessels and in subcutaneous tissue. The compounds of formula I are effective against these parasites.

The compounds of formula I are also suitable for controlling pathogenic parasites in humans, among which parasites there may be mentioned as typical representatives occurring in the alimentary tract those of the species Ancylostoma, Necator, Ascaris, Strongyloides, Trichinella, Capillaria, Trichuris and Enterobius. The compounds of this invention are also effective against parasites of the species Wuchereria, Brugia, Onchocerca and Loa of the family of the Filariidae which occur in the blood, in tissue and various organs, and, in addition, against Dracunculus and parasites of the species Strongyloides and Trichinella which infest in particular the exointestinal tract.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The compounds of formula I are administered to warm-blooded animals at rates of application of 0.01 to 50 mg/kg of body weight, and are applied to enclosed crop areas, to pens, livestock buildings or other buildings in amounts of 10 g to 1000 g per hectare.

The formulations, i.e. the compositions or preparations containing the compounds (active ingredients) of the formula I are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. The physical properties may also be improved by adding highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

The surfactants customarily employed in the art of formulation are described e.g. in "McCutcheon's Detergents and Emulsifiers Annual", MC Publishing Corp. Ridgewood, N.J., 1982, and H. Stache, "Tensid-Taschenbuch" (Handbook of Surfactants), Carl Hanser Verlag, Munich/Vienna, 1981.

The pesticidal compositions normally contain 0.01 to 95%, preferably 0.1 to 80%, of a compound of formula I, 5 to 99.99% of a solid or liquid adjuvant, and 0 to 25%, preferably 0.1 to 25%, of a surfactant.

Whereas commercial products are preferably formulated as concentrates, the end user will normally employ dilute formulations having a concentration of 1–10,000 ppm.

Accordingly, the present invention further relates to pesticidal compositions which contain, as active ingredient, a compound of formula I, together with conventional carriers and/or diluents.

The compositions may also contain further ingredients, such as stabilisers, antifoams, viscosity regulators, binders, tackifiers as well as fertilisers or other active ingredients for obtaining special effects.

| Formulation examples for active ingredients of the formula I (throughout, percentages are by weight) | | | |
|---|---|---|---|
| Wettable powders | (a) | (b) | (c) |
| compound of formula I | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| compound of formula I | 10% |
| octylphenol polyethylene glycol ether (4–5 moles of ethylene oxide) | 3% |
| calcium dodecylbenzenesulfonate | 3% |
| castor oil polygycol ether (36 moles of ethylene oxide) | 4% |
| cyclohexanone | 30% |
| xylene mixture | 50% |

Emulsions of any required concentration can be obtained from this concentrate by dilution with water.

| Dusts | (a) | (b) |
|---|---|---|
| compound of formula I | 5% | 8% |
| talcum | 95% | — |
| kaolin | — | 92% |

Ready for use dusts are obtained by mixing the active ingredient with the carriers, and grinding the mixture in a suitable mill.

| Extruder granulate | |
|---|---|
| compound of formula I | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

If the compound of formula I, or compositions containing it, are used for controlling endoparasitic nematodes, cestodes and trematodes in domestic animals and productive livestock, for example cattle, sheep, goats, horses, pigs, cats and dogs, they can be administered to the animals in both single and repeated doses. Depending on the species of animal, the individual doses are preferably administered in amounts ranging from 0.1 to 10 mg/kg of body weight. A better action is often achieved by protracted administration, or lower total doses will also suffice. The compounds, or compositions containing them, can also be added to feeds and drinks. The ready-prepared feeds contain the active ingredients preferably in a concentration of 0.005 to 0.1 percent by weight. The compositions can be administered to the animals perorally in the form of solutions, emulsions, suspensions, powders, tablets, boluses or capsules. Those compositions are prepared with the aid of e.g. conventional solid carriers such as kaolin, talcum, bentonite, sodium chloride, calcium phosphate, cotton seed flour, or liquids that do not react with the active ingredient, such as oils and other solvents and diluents that are harmless to the animal organism.

If the physical and toxicological properties of solutions or emulsions permit it, the compounds of formula I, or compositions containing them, can also be injected into animals, for example subcutaneously or by intraruminal injection, or applied to the bodies of the animals by the pour-on method. Administration by means of salt licks or molasses blocks is also possible.

BIOLOGICAL EXAMPLES

B1: Insecticidal stomach poison action against *Spodoptera littoralis*

Potted cotton plants in the 5-leaf stage are sprayed with a solution containing 3, 12.5 or 50 ppm of the test compound in acetone/water. After the coating has dried, the plants are populated with about 30 larvae (L₁ stage) of *Spodoptera littoralis*. Two plants are used for each test compound and test species. The test is carried out at about 24° C. and 60% relative humidity. Evaluations and intermediate evaluations of dead insects, growth of larvae and feeding damage are made after 24, 48 and 72 hours.

Complete kill was achieved after 24 hours with compounds 1.9, 2.3 and 3.3 at a concentration of 3 ppm.

B2: Action against plant destructive acarids: OP-sensitive *Tetranychus urticae*

16 hours before the start of the test, the primary leaves of bean plants (*Phaseolus vulgaris*) are infected with an infected piece of leaf from a mass culture of *Tetranychus urticae*. Upon removal of the piece of leaf, the plants infested with all stages of the mites are sprayed to drip point with a solution containing 0.4 ppm or 1.6 ppm of the test compound. The temperature in the greenhouse compartment is about 25° C.

The percentage of mobile stages (adults and nymphs) and of eggs is made under a stereoscopic microscope after 7 days.

Compounds 1.5, 2.3, 2.35 and 3.3 effected complete kill at a concentration of 1.6 ppm.

B3: Action against $L_1$ larvae of *Lucilia serticata*

1 ml of an aqueous suspension of test compound is mixed with 3 ml of a special larval culture medium at about 50° C. such that a homogeneous composition containing 250 ppm or 125 ppm of active ingredient is obtained. About 30 *Lucilia sericata* larvae ($L_1$) are put into each test tube containing active ingredient. A mortality count is made after 4 days. Compounds 1.5 and 2.3 effected 100% kill at a concentration of 125 ppm.

B4: Acaricidal action against *Boophilus microplus* (Biarra strain)

Adhesive tape is applied horizontally across a PVC plate so that 10 female *Boophilus microplus* ticks (Biarra strain), replete with blood, can be affixed thereto with their backs, side by side, in a row. Each tick is injected from an injection needle with 1 μl of a liquid which contains a 1:1 mixture of polyethylene glycol and acetone, in which mixture a specific amount of test compound of 1, 0.1 or 0.01 μg per tick is dissolved. Control ticks are injected with liquid containing no test compound. After this treatment, the ticks are detached from the support and kept in an insectarium at about 28° C. and 80% relative humidity until oviposition has taken place and the larvae have hatched from the eggs of the control ticks.

The activity of the test compound is determined with the $IR_{90}$, i.e. the effective dose is determined at which 9 out of 10 female ticks (90%) even after 30 days lay eggs from which larvae do not emerge. An $IR_{90}$ of 0.1 μg, is achieved with compounds 1.1, 1.4, 1.5 and 1.9.

B5: Trial with sheep infected with nematodes (*Haemonchus concortus* and *Trichostrongylus colubriformis*)

The test compound is administered in the form of a suspension with a stomach probe or by intraruminal injection to sheep which have been artificially infected with *Haemonchus concurtus* and Trichostrongylus. One to three animals are used for each dose. Each sheep is treated only once with a single dose, namely with 1 mg or 10 mg/kg of body weight. Evaluation is made after 7 days by comparing the number of worm eggs excreted in the faeces of the sheep before and after treatment.

Untreated sheep infected simultaneously and in the same manner are used as controls. In comparison with untreated and infected control groups, no nematode infestation (complete reduction of eggs in the faeces) was found in sheep which were treated with one of the compounds 1.1 and 3.3 at 1 mg of active ingredient/kg.

B6: Contact action against *Aphis craccivora*

Pea cuttings which have been infested with all development stages of the aphid are sprayed with a solution prepared from an emulsifiable concentrate formulation of the test compound and containing 50, 25 or 12.5 ppm of active ingredient. Evaluation takes place to determine the minimum concentration of a.i. where the mortality of the aphids is more than 80% after 3 days. A composition is only rated as effective at this level of activity.

Complete kill (100%) was achieved with compounds 1.3 and 3.3 at a concentration of 12.5 ppm.

B7: Larvicidal action against *Aedes aegypti*

A 0.1% solution of the test compound in acetone is pipetted onto the surface of 150 ml of water in a beaker in an amount sufficient to give concentrations of 10, 3.3 and 1.6 ppm. After the actone has evaporated, 30–40 three-day-old larvae of *Aedes aegypti* are put into the beaker containing the test compound. Mortality counts are made after 1, 2 and 3 days.

In this test, compounds 1.5 and 1.9 effected complete kill of all larvae at a concentration of 1.6 ppm after 1 day.

What is claimed is:

1. A milbemycin derivative of the formula

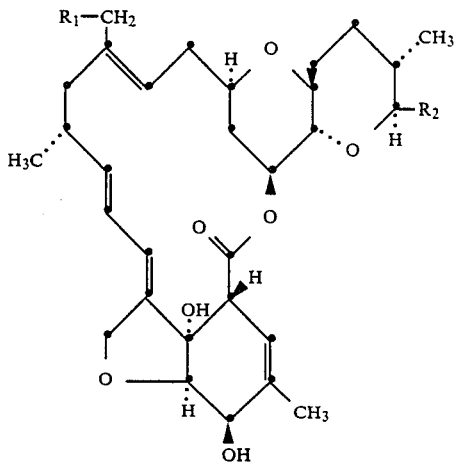

wherein
$R_1$ is $C_1$–$C_4$-alkyl, chloro, bromo, $C_1$–$C_4$-alkoxy, $C_1$–$C_4$-haloalkoxy, or $C_2$–$C_6$-hydroxyalkoxy, and $R_2$ is methyl, ethyl or isopropyl.

2. A compound of claim 1, wherein $R_1$ is $C_1$–$C_4$alkyl.

3. A compound of claim 2, wherein $R_1$ is methyl or ethyl.

4. A compound of claim 1, wherein $R_1$ is chloro or bromo.

5. A compound of claim 1, wherein $R_1$ is $C_1$–$C_4$-alkoxy, $C_1$–$C_4$-haloalkoxy or $C_2$–$C_6$-hydroxyalkoxy.

6. A compound of claim 5, wherein $R_1$ is $C_1$–$C_4$alkoxy or $C_1$–$C_4$-haloalkoxy.

7. A compound of claim 5, wherein $R_1$ is $C_2$–$C_6$hydroxyalkoxy.

8. A pesticidal composition which contains at least one compound of claim 1 and an inert carrier.

9. A method of controlling insects and pests of the order Acarina at a locus, which comprises applying to said locus a pesticidally effective amount of a compound of claim 1.

10. A method of controlling nematodes at a locus, which comprises applying to said locus a pesticidally effective amount of a compound of claim 1.

11. A method of controlling pests of animals and plants, which comprises treating said animals or plants with a pesticidally effective amount of a compound of claim 1.

12. A method of controlling ecto- and endoparasites on or in warm-blooded animals, which comprises treating said animals with a pesticidally effective amount of a compound of claim 1.

* * * * *